United States Patent [19]
Oxman et al.

[11] Patent Number: 5,718,577
[45] Date of Patent: Feb. 17, 1998

[54] DENTAL IMPRESSION TRAY WITH CHEMILUMINESCENT LIGHT SOURCE

[75] Inventors: Joel D. Oxman, Minneapolis; Cary A. Kipke, Woodbury; Bruce R. Broyles, Oakdale, all of Minn.

[73] Assignee: Minnesota Mining & Manufacturing, St. Paul, Minn.

[21] Appl. No.: 617,995

[22] Filed: Mar. 15, 1996

[51] Int. Cl.[6] .................................................. A61C 1/00
[52] U.S. Cl. .................................. 433/37; 433/214; 433/29; 362/34
[58] Field of Search ................................ 433/29, 34, 35, 433/37, 71, 214, 229; 362/34, 804

[56] References Cited

U.S. PATENT DOCUMENTS

| | | |
|---|---|---|
| 1,084,017 | 1/1914 | Lautenburg . |
| 2,239,960 | 4/1941 | Harbart ........................... 433/35 |
| 2,312,171 | 2/1943 | Jochum ........................... 433/35 |
| 3,590,003 | 6/1971 | Meyers et al. ................... 252/186 |
| 3,597,362 | 8/1971 | Bollyky et al. .................. 252/186 |
| 3,630,941 | 12/1971 | Bergmark ........................ 252/186 |
| 3,689,391 | 9/1972 | Ullman ........................... 204/159 |
| 3,749,677 | 7/1973 | Maulding ....................... 252/188.3 |
| 4,449,928 | 5/1984 | von Weissenfluh ............... 433/40 |
| 4,543,063 | 9/1985 | Cohen ............................ 433/175 |
| 4,553,936 | 11/1985 | Wang ............................. 433/37 |
| 4,740,159 | 4/1988 | Hamilton et al. ............... 433/37 |
| 4,761,136 | 8/1988 | Madhavan et al. .............. 433/214 |
| 4,790,752 | 12/1988 | Cheslak ......................... 433/37 |
| 4,867,680 | 9/1989 | Hare et al. ..................... 433/37 |
| 4,867,682 | 9/1989 | Hammesfahr et al. ........... 433/37 |
| 4,888,489 | 12/1989 | Bryan ........................... 250/504 H |
| 4,916,169 | 4/1990 | Boardman et al. ............... 522/27 |
| 5,030,093 | 7/1991 | Mitnick .......................... 433/164 |
| 5,127,829 | 7/1992 | Nordquist ........................ 433/35 |
| 5,145,886 | 9/1992 | Oxman et al. ................... 522/66 |
| 5,147,204 | 9/1992 | Patten et al. ................... 433/229 |
| 5,171,081 | 12/1992 | Pita et al. ...................... 362/34 |
| 5,179,186 | 1/1993 | Muller et al. ................... 528/49 |
| 5,277,173 | 1/1994 | Cantele .......................... 362/34 |
| 5,316,473 | 5/1994 | Hare .............................. 433/29 |
| 5,321,587 | 6/1994 | Fujita ............................. 362/34 |
| 5,487,662 | 1/1996 | Kipke et al. .................... 433/37 |
| 5,509,801 | 4/1996 | Nicholson ....................... 433/35 |

FOREIGN PATENT DOCUMENTS

| | | |
|---|---|---|
| 0 170 219 | 5/1986 | European Pat. Off. . |
| 0 173 085 | 5/1986 | European Pat. Off. . |
| 0 269 071 | 1/1988 | European Pat. Off. . |
| 0 255 286 | 3/1988 | European Pat. Off. . |
| 0 460 478 | 11/1991 | European Pat. Off. . |

*Primary Examiner*—Ralph Lewis
*Attorney, Agent, or Firm*—Gary L. Griswold; Walter N. Kirn; James D. Christoff

[57] ABSTRACT

A dental impression tray has wall portions defining at least one channel for receiving a quantity of photocurable dental impression material. At least one of the wall portions is located next to the chamber and is made of a material that transmits electromagnetic actinic radiation. The tray also includes a chamber for receiving a chemiluminescent composition. Light emitted from the chemiluminescent composition induces the curing of the impression material in a uniform manner along the length of the channel.

22 Claims, 2 Drawing Sheets

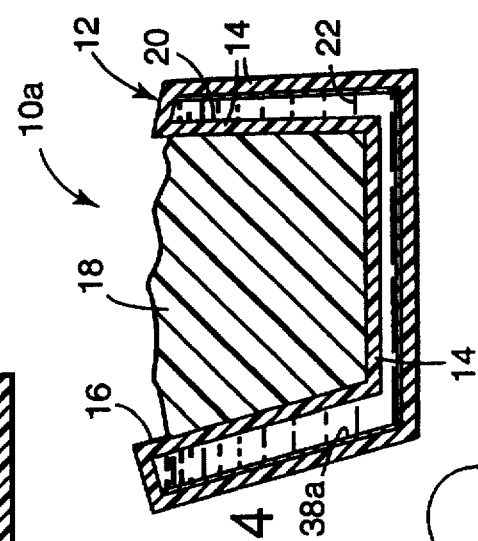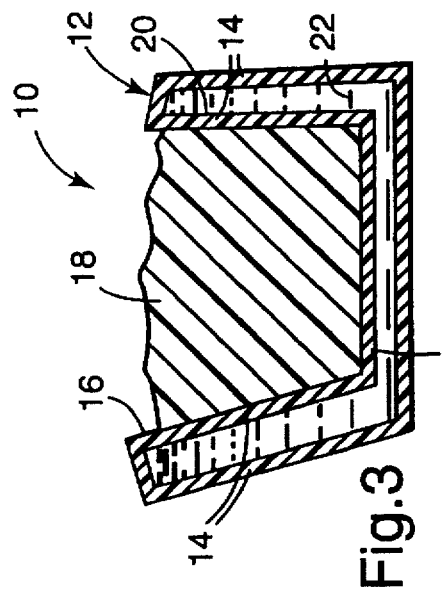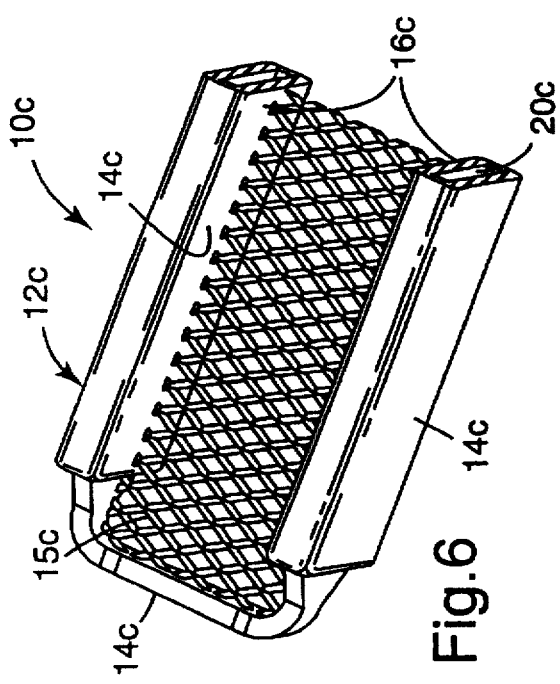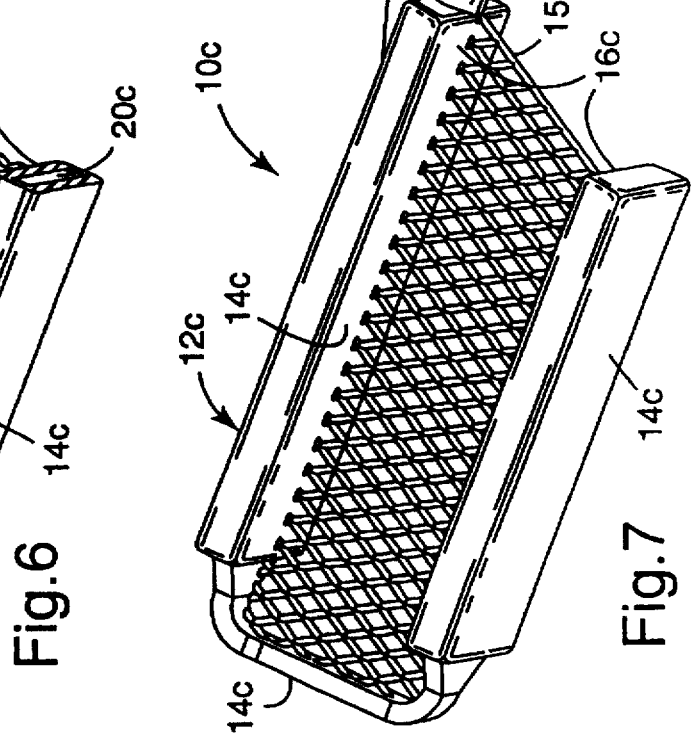

DENTAL IMPRESSION TRAY WITH CHEMILUMINESCENT LIGHT SOURCE

BACKGROUND OF THE INVENTION

1. Field of the Invention

This invention relates to a dental impression tray adapted for use with impression material that cures upon exposure to light. More particularly, this invention relates to a dental impression tray having a chemiluminescent light source for inducing the curing of photopolymerizable impression material.

2. Description of the Related Art

Dental impression trays are used to hold impression material for making a model of a patient's tooth and oral tissue anatomy so that a crown, bridge, denture, veneer, restoration or the like can be made. A typical procedure involves placing a quantity of impression material in an open trough or channel of the tray and then pressing the tray onto the dental arch of the patient. The impression material is allowed to cure while in the oral cavity. The tray with the impression material is then removed from the oral cavity, and the impression material is used to prepare a positive model that replicates the selected area of the patient's arch.

Most conventional dental impression materials are made by mixing two components immediately before the impression is taken. Mixing of the components initiates a polymerization reaction that eventually causes the material to harden and cure. Consequently, as soon as the components are mixed, it is important for the dental practitioner to promptly deliver the tray to the oral cavity and accurately position the impression material relative to the selected area of the dental arch so that an accurate impression can be made.

Typically, a manufacturer of dental impression material provides recommended guidelines to the practitioner that specify both a working time and a setting point time to be followed when using the material. The working time is determined by the composition oft he polymeric system and is the total time allowed for mixing the components, placing the mixed components in the tray, delivering the tray to the oral cavity and accurately seating the impression material onto desired areas of the patient's dental arch. The setting point time relates to the degree of curing of the impression material, and represents the total time that should elapse (after the components are mixed) before the tray is removed from the oral cavity in order to ensure that the impression material has cured to a degree sufficient that the impression will not be distorted as the tray is removed from contact with the dental arch.

A variety of dental impression materials are currently available that polymerize upon mixing of two components. Such materials include, for example, alginates, polysulfides, polyethers and silicones. Recommended working times and setting point times for such materials are often in the range of about 1.25 to 7 minutes and 1.5 to 10 minutes respectively.

Unfortunately, dental impression materials that begin to polymerize upon mixing are not entirely satisfactory, because taking of the impression should be completed within a predetermined amount of time. If, for example, the procedure is interrupted by the dentist or by the patient for some unforeseen reason, the impression material may cure to such a degree that it is unusable before the procedure can be resumed. Another problem associated with such impression materials relates to the differences in recommended working times and setting point times for the variety of materials that are currently available, since a dental practitioner who has long used one type of material may fail to follow the manufacturer's recommended working time and setting point time for another material that is substituted.

For many impression materials that cure upon mixing, the length of the working time and the setting point time are determined by the amount of catalyst in the mixture. As a consequence, one who attempts to decrease the setting point time by increasing the catalyst concentration may be frustrated because the working time may also be unduly shortened. Conversely, an attempt to increase the working time may result in lengthening the setting point time by an unsatisfactory amount.

Certain impression materials that are mixed in the dental office are also unsatisfactory in instances where the mixing method (such as hand spatulalion) introduces air bubbles into the mixture. Air bubbles may cause surface imperfections in the finished impression. In addition, it should be noted that mixing of the materials by hand spatulation is inherently somewhat time consuming.

It has been suggested that the use of photopolymerizable dental impression materials overcomes the disadvantages often associated with impression materials that are curable when mixed. Photopolymerizable impression materials include a photocatalyst and/or a photoinitiator that initiates polymerization of the impression material upon exposure to an appropriate wavelength of light. In the absence of such a light source, the impression material will remain substantially unpolymerized for a relatively long period of time so that the dental practitioner can ensure that the tray is accurately positioned before the impression material cures. Examples of photo curable materials are set out in U.S. Pat. Nos. 5,179,186, 5,145,886, 4,761,136, 4,543,063, 4,740,159 and 4,916,169 and European patent application publication nos. 0460478, 0269071, 0255286, 0173085 and 0170219.

Photopolymerizable impression materials also provide a potential advantage in instances where the tray is accurately placed in the mouth in a relatively short amount of time. In such instances, the light source can be immediately activated to begin curing of the impression material, so that the overall time necessary to complete the impressioning procedure can be reduced. By contrast, a practitioner using an impression material that immediately begins to cure upon mixing is generally unable to shorten the time necessary for completion of the impressioning procedure even when the tray is quickly placed in the oral cavity because the polymerization reaction will proceed at the same rate.

However, known dental impression trays and procedures for using such trays with photopolymerizable dental impression materials are generally unsatisfactory. Some practitioners have attempted to use photopolymerizable impression material by placing the material in a transparent tray and directing an incandescent source of light through the tray and into the impression material to initiate polymerization. Such a procedure is described, for example, in U.S. Pat. No. 4,867,682.

In the past, the light source suggested for use in curing photocurable impression materials is often the same dental material curing apparatus that is commonly found in dental offices for curing adhesives, sealants and restorative materials. Such curing apparatus are described, for example, in U.S. Pat. Nos. 4,888,489 and 5,147,204 (both of which are assigned to the assignee of the present invention) and have a rigid light guide made of a bundle of optical fibers that are fused together. Unfortunately, it is difficult to use such a light guide in the oral cavity when a dental impression tray is also in place in the oral cavity, since space in the oral cavity is somewhat limited and the patient may experience discomfort in an attempt to open his or her jaws to an extent sufficient to enable the light guide to be positioned next to various regions of the tray. The practitioner should also take care to avoid bumping the tray with the light guide so that the impression is not distorted. Another disadvantage with such practice is that the hand-held light source may not be directed toward all regions of the tray, resulting in a failure of the impression material to cure in such regions.

U.S. Pat. Nos. 4,553,936 and 4,790,752 describe dental impression trays having a portal or socket for detachably receiving the light guide of dental material curing apparatus. The trays in certain embodiments of these patents have reflective surfaces or other structure to facilitate directing the light to various regions of the tray. However, such trays are disadvantageous in that the light source is relatively expensive and the light guide must be sterilized along with the tray between uses.

Another problem associated with prior methods and devices for curing photocurable impression material involves the amount of useful light energy available from conventional light sources and the resultant time necessary to obtain the satisfactory cure. It has been observed that curing times using photocurable dental impression material and conventional light sources are often relatively lengthy, resulting in a nuisance and expense to both the dental practitioner and the patient. Such relatively lengthy curing times may be due to the variation in intensity of the light that reaches various regions of the tray. In addition, incandescent lamps emit light over a broad range of wavelengths, much of which is wasted since it is not absorbed by the photoinitiator or photocatalyst.

U.S. Pat. Nos. 5,487,662 and 5,316,473 describe dental impression trays that include a self-contained source of light. In U.S. Pat. No. 5,487,662, the source of light is preferably a series of solid state emitters such as light emitting diodes that are connected to a battery or other source of power. Such trays are an advantage in that the light source may be positioned in close proximity to the impression material, and the need for a remote light source is avoided.

The solid state emitters described in U.S. Pat. No. 5,487,662 preferably provide light having wavelengths in a range that is known as the therapeutic window for tissue transmission. The preferred therapeutic window range extends from about 630 nanometers to about 980 nanometers. Light having wavelengths in the therapeutic window provides better penetration of soft oral tissue and may provide improved curing of impression material in gingival and sub-gingival regions in comparison to light having wavelengths near the center of the visible spectrum. Such light also penetrates the impression material more deeply because the light is scattered less than light having shorter wavelengths.

However, dental impression trays having a self-contained electric light source are somewhat expensive due to specialized solid state emitters, bulbs or other materials that are used in construction of the trays. Moreover, the weight of the batteries or, alternatively, electrical cords that interconnect the tray and a power source may hinder the procedure of taking the impression and may create a distortion in the impression material as it is cured. The effects of even relatively small amounts of additional weight are often amplified because the batteries or cords are typically located outside of the oral cavity. In such construction, the additional weight functions as a lever or moment arm and as a result the likelihood of unintentional movement of the portion of the tray that is within the oral cavity and resulting distortion of the impression material is increased.

A dental impression tray having a water jacket is described in U.S. Pat. No. 1,084,017. Trays of this general type are often used with hydrocolloid impression material, and are connected by two tubes to a water bath having a controller that maintains the water at a certain temperature. Heated water from the water bath passes through the tray where the thermal energy of the water is transferred to a tray channel and consequently to the impression material for curing the latter. The tray is made of a metallic material to facilitate the transfer of heat into the impression material.

SUMMARY OF THE INVENTION

The present invention overcomes the above-noted disadvantages by provision of a dental impression tray having a chemiluminescent light source. The tray comprises a body having wall portions defining at least one channel for receiving a quantity of photocurable dental impression material. The tray also includes a chamber for receiving a chemiluminescent composition and an inlet opening in communication with the chamber for admitting chemiluminescent composition into the chamber. The tray also includes a closure for closing the inlet opening. At least one of the wall portions is located next to the chamber and is made of a material that transmits electromagnetic actinic radiation.

The present invention is also directed toward an impression tray that comprises a body having wall portions defining at least one channel for receiving a quantity of photo curable dental impression material. The tray includes a chamber and a chemiluminescent light source received in the chamber. At least one of the wall portions is located next to the chamber and is made of a material that transmits electromagnetic actinic radiation.

Advantageously, the tray in various embodiments of the invention enables the chemiluminescent light source to be in close proximity to the dental impression material and enables the emitted light to be distributed uniformly to various regions of the dental impression material for more efficient curing. The relatively small additional weight presented by the chemiluminescent light source is preferably distributed along the tray and as such does not present a moment arm to any significant extent. The tray is also relatively inexpensive to manufacture and may be constructed for either single use or multiple uses as desired.

These and other aspects of the invention are described in more detail in the description that follows and in the accompanying drawings.

BRIEF DESCRIPTION OF THE DRAWINGS

FIG. 3 is an enlarged side cross-sectional view taken along lines 3—3 in FIG. 2, and additionally showing a quantity of photocurable impression material received in a channel of the tray;

FIG. 4 is a view somewhat like FIG. 3 but in accordance with another embodiment of the invention;

FIG. 6 is a perspective view of a dental impression tray according to still another embodiment of the invention; and FIG. 7 is a perspective cross-sectional view of the tray illustrated in FIG. 6.

DETAILED DESCRIPTION OF THE PREFERRED EMBODIMENTS

Figure 1:
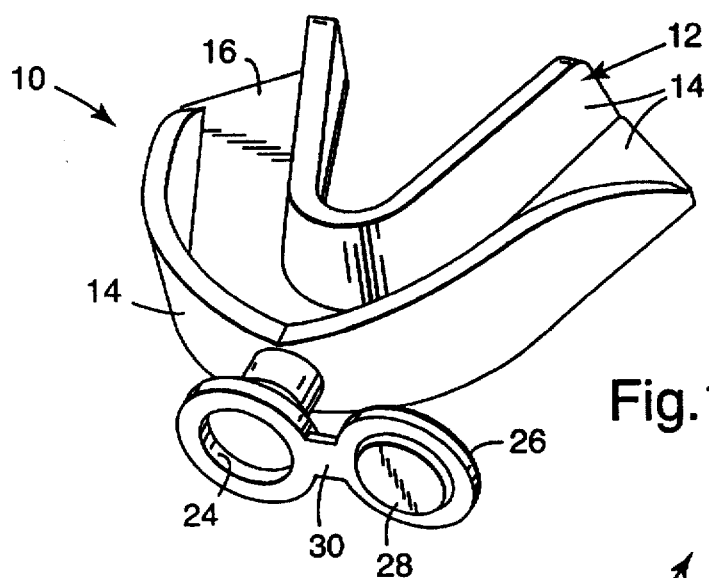
FIG. 1 is a perspective view of a dental impression tray constructed in accordance with one embodiment of the present invention.
Figure 2:
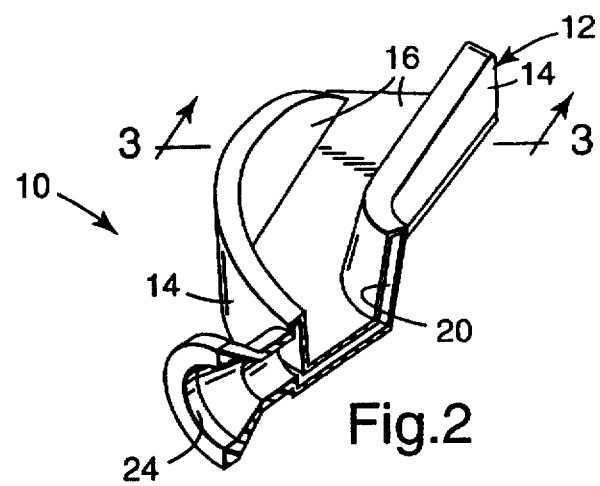
FIG. 2 is a perspective cross-sectional view of the tray shown in FIG. 1 and illustrating an inner chamber of the tray.

A dental impression tray according to one embodiment of the present invention is designated broadly by the numeral 10 in FIGS. 1–3. The tray 10 includes a body 12 having an overall generally U-shaped configuration in plan view that is adapted to match the overall, generally U-shaped configuration of the patient's upper or lower dental arch. The body 12 includes integrally connected wall portions 14 that define a channel 16.

The channel 16 is adapted to receive a quantity of photocurable dental impression material 18, (as shown in FIG. 3) for making an impression of the patient's upper or lower dental arch. The wall portions 14 include spaced apart inner and outer bottom wall portions and spaced apart inner and outer side wall portions, and the bottom wall portions and the side wall portions together provide an overall generally U-shaped configuration when viewed in directions perpendicular to the length of the channel 16.

The tray 10 also includes an internal chamber 20 (FIGS. 2 and 3) for receiving a chemiluminescent light source composition 22 (see FIG. 3). The chamber 20 is located between the spaced apart inner and outer side wall portions and the spaced apart inner and outer bottom wall portions. Preferably, the chamber 20 extends substantially the entire length of the channel 16, the entire height of the side wall portions and the entire width of the bottom wall portions in order to surround the impression material 18 on three sides as illustrated in FIG. 3 in each region along the length of the channel 16.

The wall portions 14 that are located next to the chamber 20 are made of a material that transmits electromagnetic actinic radiation suitable to induce curing of the impression material 18 in the channel 16. Preferably, the body 12 including all of the wall portions 14 are integrally made of a rigid, transparent synthetic resinous material such as polycarbonate or clarified polypropylene. The material preferably has sufficient rigidity to avoid deformation or flexing of the wall portions 14 as the impression is taken.

The tray 10 also includes an inlet port having an inlet opening 24 (FIGS. 1 and 2) that is in communication with the chamber 20 for admitting a chemiluminescent composition into the chamber 20. As shown in FIG. 1, an optional tethered closure 26 is connected to the inlet port by a living hinge 30. The closure 26 includes a stopper portion 28 having a diameter approximately equal to the diameter of the opening 24. When the closure 26 is swung in an are about the hinge 30 toward the inlet port, the stopper portion 28 is received in the opening 24 to close the latter and prevent escape of the chemiluminescent composition 22.

The chamber 20 is filled with the chemiluminescent composition 22 from a dispenser whenever curing of the impression material 18 is desired. Preferably, the dispenser includes two reservoirs that each contain one component of the chemiluminescent composition 22. Suitable dispensers include, for example, dual chamber hand operated or electrically powered dispensers that are operable to dispense quantities of each of the two chemiluminescent components under pressure to the chamber 20. Preferably, the dispenser includes a static mixing element located downstream of outlets of the reservoirs to ensure that the two components are thoroughly mixed before entering the chamber 20 of the tray 10.

Preferably, the inlet port includes a vent passageway (not shown) that is either part of or is located next to the opening 24 so that air in the chamber 20 can readily escape as the chamber 20 is filled with the chemiluminescent composition 22. The inlet port also optionally includes a small overflow reservoir connected to the vent passageway to contain a limited accumulation of the chemiluminescent composition 22 after the chamber 20 is fried but before operation of the dispenser is interrupted. The reservoir helps avoid spilling of the composition 22 from the tray 10 once the chamber 20 is full.

For purposes of the present invention, chemiluminescence is the emission of electromagnetic radiation of wavelength between about 250–1400 nanometers by means of a chemical reaction. Chemiluminescence is defined as the emission of light, from at least one molecule, by means of a chemical reaction. A chemiluminescent reaction results in the formation of an excited state molecule that is capable of direct light emission or capable of energy transfer to at least one other molecule that emits light or generates a photoinitiator. Preferred wavelength ranges for light emission are in the UV range (250–400 nm), the visible range (400–800), the near IR range (700–1400).

Typical chemiluminescence compositions or systems involve the reaction of two reactive species, such as the reaction of hydrogen peroxide with oxalate compounds. These reactive species are generally provided as two separate reaction components that are mixed together at the time of use.

The components used to provide chemiluminescent light may be comprised of those chemicals known in the art to create light chemically upon mixing.

Preferred systems are the two-component chemistries comprising an oxalate component, a peroxide component together with a fluorescer and a catalyst. Examples of such include those disclosed in U.S. Pat. No. 5,281,347 and 3,689,391, the disclosures of which are incorporated by reference. These systems may include additional fluorescent species, catalysts, solvents, accelerators and additive systems.

Chemiluminescent light can be "tuned" to provide light at distinct wavelength regions via an excited state energy transfer reaction to specific acceptor molecules. A donor molecule is defined as an excited state molecule that is formed from a chemiluminescence reaction. This molecule may directly emit light or transfer energy to an acceptor molecule. Acceptor molecules may be molecules that accept energy from a donor molecule and then emit light or generate photoinitiators. Examples of acceptor molecules that emit light throughout the visible region are described in, e.g. U.S. Pat. No. 3,597,362 and U.S. Pat. No. 3,749,677, and examples of acceptor molecules that emit light throughout the near infrared region are described in, e.g. U.S. Pat. No. 3,630,941 and U.S. Pat. No. 3,590,003, the disclosures of which are incorporated herein by reference. Light emission from a chemiluminescent reaction may provide advantages, in comparison to solid state light sources, for photopolymerization reactions. Light emission from a chemiluminescent reaction can be controlled through use of an acceptor molecule or a mixture of acceptor molecules to provide light that overlaps with the absorption region of a photoreactive molecule that is capable of initiating photopolymerization. Although solid-state light sources such as lasers, laser diodes, and light-emitting diodes provide light in the UV, visible, and near infrared energy regions, there are regions within this wavelength range (250–1400 nm) that cannot readily or currently be accessed using these solid-state light sources.

Other light sources (e.g. tungsten, mercury vapor, xenon lamps, etc.) provide a broad light emission in the UV, visible, and near infrared regions, but may be inefficient for photopolymerization reactions because only a small wavelength region of the emitted light is utilized by the light absorbing photoinitiator. With such light sources, filters may be used to select the desired wavelength while eliminating the ineffective wavelength of light. Chemiluminescent light sources, on the other hand, may be selected that have single, multiple, broad, or narrow light emission spectra, so that more of the emitted light is utilized in the photopolymerization process. A narrow emission spectrum is a region of light that is comparable to the absorption spectrum region of the photoinitiator molecule. Typical photoinitiator molecules have an absorption spectrum range of about 100 nm. Suitable acceptor molecules that emit light in a chemiluminescent reaction have an emission spectrum range of about 100 nm. Preferably, the chemiluminescent emission spectrum is substantially, equal to or encompassed by the photoinitiator absorbance spectrum. Thus, preferably most of the radiation emitted by the chemiluminescent reaction is absorbed by the photoinitiator molecule.

The dental impression material to be polymerized may be any suitable photopolymerization material, such as free-radically reactive materials, cationic polymerization materials, charge transfer polymerization reactive materials, hydrosilation reactive materials or photocyloaddition reactive polymerization materials. Typically, many of these materials incorporate a separate chemical initiator that is activated by the light emitted from the chemiluminescent light source. Examples of photocurable materials are set out in U.S. Pat. Nos. 5,179,186, 5,145,886, 4,761,136, 4,543, 063, 4,740,159 and 4,916,169 and European patent application publication nos. 0460478, 0269071, 0255286, 0173085 and 0170219.

The polymerizable material may be selected from one or more photopolymerizable materials, including photopolymerizable materials that cure through different cure mechanisms. Such mixtures of photopolymerizable materials are sometimes referred to as hybrid curing photopolymerizable materials. The photopolymerizable material may additionally utilize multiple cure mechanisms for the complete curing of the photopolymerizable material system. For example, heat may be utilized to cure a free radical curable component, while the chemiluminescent light source may be used for the cationic curable component of a hybrid system. Additionally, multiple wavelengths of light may be utilized for curing different aspects of a multi-component photopolymerizable material system.

Additional information regarding chemiluminescent compositions and photopolymerizable materials is set out in copending U.S. patent application Ser. No. 08/617,528 entitled "Photopolymerization Reactions Induced by Chemiluminescence" filed on even date herewith and incorporated by reference herein.

In a preferred use of the tray 10, a quantity of photocurable impression material (such as material 18) is placed in the channel 16 of the tray 10. Next, the tray 10 is placed in the oral cavity of the patient in such a manner that the teeth and adjacent portions of the gingiva are embedded in the impression material. Once the practitioner is satisfied with the position of the tray 10, a quantity of mixed chemiluminescent composition (such as composition 22) is admitted into the chamber 20 by placing the outlet end of the dispenser into the inlet port. After the chamber 20 is filled or substantially filled with the composition, the dispenser is withdrawn from the inlet port and the closure 26 is closed to seal the opening 24. The tray 10 is removed from the oral cavity once the impression material has set.

A dental impression tray 10a according to another embodiment of the invention is illustrated in FIG. 4. The tray 10a is substantially identical to the tray 10 except for the differences noted below. In FIG. 4, elements identified with numerals lacking the letter "a" designation are the same as like-numbered elements depicted in FIG. 3.

However, the tray 10a is covered with a layer of reflective material 38a on the inner surface of the outer side wall portions 14 and outer bottom wall portions 14 to reflect and facilitate distribution of chemiluminescent light into the impression material 18 in the channel 16. As an alternative, the layer of reflective material may be placed over the outer surface of the outer side wall portions 14 and outer bottom wall portions 14 instead of on such inner surfaces. Suitable reflective materials include barium sulfate or magnesium oxide deposits, or metallic foils.

Figure 5:
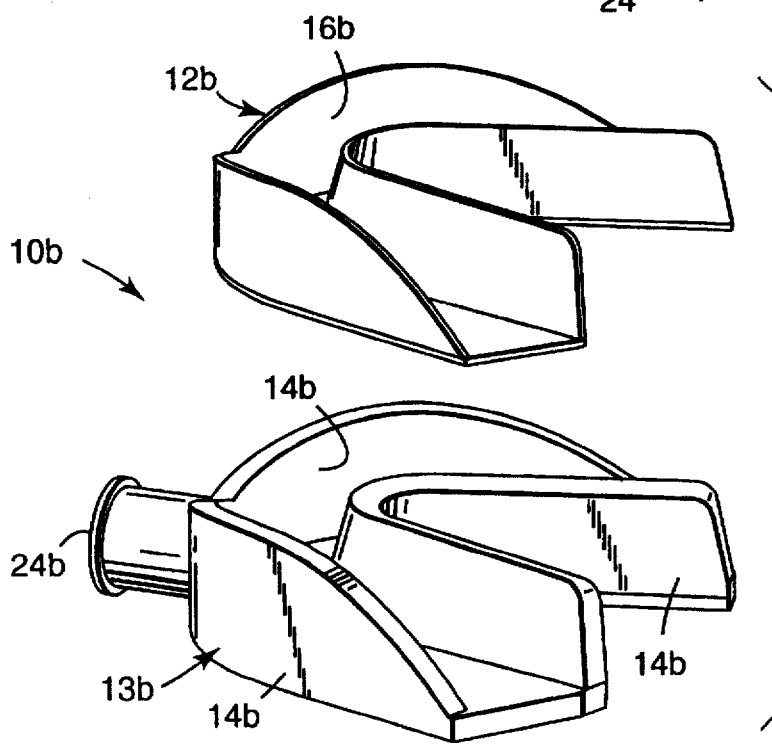
FIG. 5 is an exploded, perspective view of a dental impression tray according to yet another embodiment of the invention.

A dental impression tray 10b according to another embodiment of the invention is shown in FIG. 5. The tray 10b in this instance is an assembly that includes a body 12b and a container 13b that is detachably connected to the body 12b. The body 12b and the container 13b are preferably each integrally made of a rigid, clear synthetic resinous material that transmits electromagnetic actinic radiation. The body 12b has a channel 16b adapted to receive a quantity of photocurable dental impression material (not shown).

The container 13b is somewhat similar to the body 12 described above, and includes spaced apart wall portions 14b that define an internal chamber similar to the chamber 20. The container 13b has an inlet port with an opening 24b identical to the opening 24 for admitting a chemiluminescent composition into the chamber 20b when desired. Although not shown, the tray 10b includes a tethered closure similar to the closure 26 for closing the opening 24b.

The outer surfaces of the body 12b are complemental in shape and size to the inner surfaces defining a U-shaped channel of the container 13b. Consequently, the chamber of the container 13b surrounds the body 12b on three sides so that light emitted from the chemiluminescent composition is transmitted through the wall portions of the container 13b and through the wall portions of the body 12b, and ultimately to the impression material in the channel 16b.

The tray 10b may be an advantage in certain instances where the dental practitioner sends the impression to a remote laboratory that is located some distance from the dental office. In such an instance, the body 12b can be separated from the container 13b and shipped along with the cured impression material to the remote laboratory. The container 13b is retained in the dental office and may be cleaned, sterilized and reused. Such construction is an advantage because a number of inexpensive bodies identical to body 12b can be retained on hand in the dental office, while only a few containers such as container 13b need be purchased. Optionally, the body 12b may be intended for single use only and may be shipped by the manufacturer with a preloaded quantity of photocurable dental impression material in the channel 16b.

A dental impression tray 10c that is constructed in accordance with yet another embodiment of the invention is illustrated in FIGS. 6–7. The tray 10c includes a body 12c having a configuration adapted to take an impression of a portion of both the patient's upper and lower dental arch, such as the patient's right side upper and lower dental arches or the patient's left side upper and lower dental arches. The body 12c includes side wall portions 14c and a bottom wall portion 15c that extends along the length at the middle of the inner side wall portion 14c.

The side wall portions 14c are hollow and present a chamber 20c for receiving a quantity of chemiluminescent composition. The side wall portions 14c are made of a material that transmits actinic electromagnetic radiation. Optionally, a reflective material is provided along an inner or outer surface of the side wall portion 14c that defines the outer side surfaces of the chamber 20c.

The bottom wall portion 15c together with the side wall portions 14c define a pair of channels 16c, 16c. The upper channel 16c is adapted to receive a quantity of photocurable dental impression material for taking an impression of a portion of the patient's upper arch. Similarly, the lower channel 16c is adapted to receive a quantity of photocurable dental impression material for taking an impression of a portion of the patient's lower dental arch at the same time that an impression is taken of the overlying dental arch portion.

Preferably, the bottom wall portions 15c are made of a material that transmits light from the chamber 20c, such as a mesh made of gauze or a clear, flexible synthetic resinous material. Optionally, the mesh can be made of optical fibers having discontinuous side surfaces or other structure that directs a portion of the light traveling through the fibers into the underlying or overlying regions of the impression material. As another option, the bottom wall portions 15c may be made of a gauze material that is interwoven with a plurality of such optical fibers.

Many variations of the invention are possible. For example, a number of other closures may be provided in place of the closure described above. As one alternative, the closure may be in the form of a relatively simple plug or threaded cap. As another alternative, the inlet port may have two passageways, one for introduction of the chemiluminescent composition and the other for venting air from the chamber, and the closure may comprise a plug having two projections that are sealingly received simultaneously in respective passageways. As another alternative, the closure may include a passageway having a check valve that automatically opens under the influence of a filling tube located on the outlet end of a dispenser. Optionally, the chamber may be preloaded by the manufacturer with one component of the chemiluminescent composition, such that the dental practitioner need only add a second component whenever light is desired.

As another example, the inlet port and the closure may be omitted and the chamber may instead be preloaded with both components of the chemiluminescent composition and permanently sealed. The two components are kept initially separate from one another, but mixed together when desired to provide light. As one option, one component of the chemiluminescent composition may be initially contained in microcapsules by a microencapsulation process, and the microcapsules are broken when the body is shaken in order to mix the components together. As another option, a rupturable or removable barrier may be provided between different regions of the chamber to initially separate the components. The barrier is optionally connected to a knob or handle of the tray and is ruptured when the knob or handle is turned or otherwise moved relative to the tray body.

As another example, the chamber for the chemiluminescent composition may be contained and defined by a flexible, bag or pouch-like container adapted for single or multiple uses. Such a pouch-like container may be detachably connected to the tray body by suitable retaining clips, hook and loop fasteners or other devices. Optionally, the body may be provided with a recess for receiving the pouch-like container. The pouch-like container may be U-shaped in plan view to extend along the length of the channel, and may optionally present a U-shaped configuration in reference planes perpendicular to the length of the channel in order to surround the latter on three sides. If the container has only a single chamber and is adapted for single use, the container may include a rupturable barrier that initially separates the two chemiluminescent components and ruptures when the container is flexed in order to mix the component and initiate the chemiluminescent reaction. If the container is adapted for reuse, the container may have a closure similar to the closures described above.

A number of other variations of the invention are also possible. Consequently, the scope of the invention should not be deemed limited to the embodiments described above in detail, but only by a fair scope of the claims that follow along with their equivalents.

We claim:

1. A dental impression tray comprising a body having wall portions defining at least one channel for receiving a quantity of photocurable dental impression material, said channel having a configuration adapted to match the configuration of at least part of a patient's oral cavity, said tray also including a chamber and a chemiluminescent composition received in said chamber, at least one of said wall portions being located next to said chamber and being made of a material that transmits electromagnetic actinic radiation.

2. The dental impression tray of claim 1, wherein said chamber is enclosed.

3. The dental impression tray of claim 2, .wherein said tray includes an inlet opening in communication with said chamber, and a closure for closing said inlet opening.

4. The dental impression tray of claim 1, wherein said chemiluminescent composition is a pourable liquid.

5. The dental impression tray of claim 1, wherein said body includes said chamber.

6. The dental impression tray of claim 5, wherein said body is integrally made of a synthetic resinous material.

7. The dental impression tray of claim 1, wherein said tray includes a container containing said chamber, and wherein said container is detachably connected to said body.

8. The dental impression tray of claim 7, wherein said chamber is enclosed by said container, and wherein said container includes an inlet opening in communication with said chamber and a closure for closing said inlet opening.

9. The dental impression tray of claim 8, wherein said body includes bottom wall portions and side wall portions, and wherein said container includes bottom wall portions and side wall portions complemental in configuration to said bottom wall portions and said side wall portions of said body respectively.

10. The dental impression tray of claim 7, wherein said body is made of a rigid synthetic resinous material.

11. The dental impression tray of claim 1, wherein said tray includes at least one reflective surface next to said chamber for reflecting light toward said channel.

12. The dental impression tray of claim 1, wherein said body has wall portions defining upper and lower channels for taking an impression of a patient's upper and lower dental arch respectively.

13. A dental impression tray comprising a body having wall portions defining at least one channel for receiving a quantity of photocurable dental impression material, said tray also including a chamber for receiving a chemiluminescent composition and an inlet opening in communication with said chamber for admitting chemiluminescent composition into said chamber, said tray also including a closure for closing said inlet opening, at least one of said wall portions being located next to said chamber and being made of a material that transmits electromagnetic actinic radiation, said tray including a quantity of chemiluminescent composition received in said chamber.

14. The dental impression tray of claim 13, wherein said body includes said chamber.

15. The dental impression tray of claim 13, wherein said body is integrally made of a synthetic resinous material.

16. The dental impression tray of claim 13, wherein said tray includes at least one reflective surface next to said chamber for reflecting light toward said channel.

17. The dental impression tray of claim 13, wherein said body has wall portions defining upper and lower channels for taking an impression of a patient's upper and lower dental arch respectively.

18. The dental impression tray of claim 13, wherein said closure includes a tethered plug.

19. The dental impression tray of claim 13, wherein said channel has a generally U-shaped configuration in plan view for taking an impression of a full dental arch.

20. The dental impression tray of claim 13, wherein said channel has a configuration for taking an impression of only a portion of a dental arch.

21. A dental impression tray comprising a body having wall portions defining at least one channel for receiving a quantity of dental impression material, said tray also including a chamber for receiving a chemiluminescent composition and an inlet opening in communication with said chamber for admitting chemiluminescent composition into said chamber, said tray also including a closure for closing said inlet opening, at least one of said wall portions being located next to said chamber and being made of a material that transmits electromagnetic actinic radiation, wherein said tray includes a container containing said chamber, and wherein said container is detachably connected to said body.

22. The dental impression tray of claim 21, wherein said body includes bottom wall portions and side wall portions, and wherein said container includes bottom wall portions and side wall portions complemental in configuration to said bottom wall portions and said side wall portions of said body respectively.

* * * * *